United States Patent [19]

Nakao et al.

[11] Patent Number: 4,843,075

[45] Date of Patent: Jun. 27, 1989

[54] BENZOTHIOPYRANO[4,3-C]PYRIDAZINE COMPOUNDS, METHODS FOR PREPARING SAID COMPOUNDS AND USES OF SAID COMPOUNDS

[75] Inventors: Toru Nakao, Nakatsu; Minoru Kawakami, Fukuoka; Yasuto Morimoto, Nakatsu; Shuzo Takehara, Nakatsu; Tetsuya Tahara, Nakatsu, all of Japan

[73] Assignee: Yoshitomi Pharmaceutical Industries, Ltd., Osaka, Japan

[21] Appl. No.: 87,569

[22] PCT Filed: Dec. 27, 1986

[86] PCT No.: PCT/JP86/00672

§ 371 Date: Jul. 17, 1987

§ 102(e) Date: Jul. 17, 1987

[87] PCT Pub. No.: WO87/04162

PCT Pub. Date: Jul. 16, 1987

[30] Foreign Application Priority Data

Jan. 10, 1986 [JP] Japan .................................. 61-3904

[51] Int. Cl.$^4$ ..................... A61K 31/50; C07D 495/04
[52] U.S. Cl. ..................... 514/248; 544/234; 549/23
[58] Field of Search ................ 514/248; 544/234, 239; 548/374, 375

[56] References Cited

PUBLICATIONS

Lombardino et al., J. Med. Chem. 24, p. 830 (1981).

Primary Examiner—Donald G. Daus
Assistant Examiner—E. Bernhardt
Attorney, Agent, or Firm—Wenderoth, Lind & Ponack

[57] ABSTRACT

A benzothiopyrano[4,3-c]pyridazine compound of the formula:

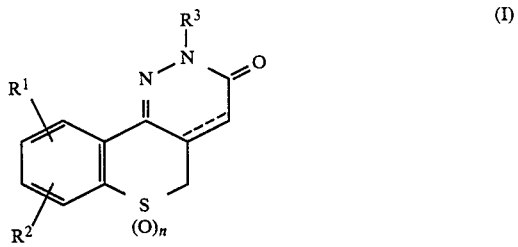

(I)

wherein $R^1$ and $R^2$ are the same or different and each is hydrogen, halogen, trifluoromethyl, hydroxy, amino, nitro, cyano, $C_{1-4}$ alkyl, $C_{1-4}$ alkoxy or $C_{2-5}$ alkanoylamido, $R^3$ is hydrogen, $C_{1-8}$ alkyl, hydroxy-$C_{1-4}$ alkyl, $C_{2-5}$ alkanoyloxy-$C_{1-4}$ alkyl, pyridyl, aryl, aryl-$C_{1-4}$ alkyl, or aryl or aryl-$C_{1-4}$ alkyl substituted by at least one substituent selected from the group consisting of halogen, trifluoromethyl, hydroxy, hydroxy, amino, nitro, cyano, $C_{1-4}$ alkyl, $C_{1-4}$ alkoxy and $C_{2-5}$ alkanoylamido on the aromatic ring, n is 0, 1 or 2, and the bond═ between the 4-position and the 4a-position is a single bond or double bond, a method for production thereof and a use thereof.

The compounds possess anti-anxietic activity and are useful as drugs.

5 Claims, No Drawings

BENZOTHIOPYRANO[4,3-C]PYRIDAZINE COMPOUNDS, METHODS FOR PREPARING SAID COMPOUNDS AND USES OF SAID COMPOUNDS

TECHNICAL FIELD

The present invention relates to novel and pharmaceutically useful benzothiopyrano[4,3-c]pyridazine compounds, methods for preparing said compounds and pharmaceutical compositions containing said compounds.

BACKGROUND ART

European Patent Application No. 124314A discloses such compounds possessing potent cardiotonic and antihypertensive activities as 2,4,4a,5-tetrahydro-7-(1H-imidazol-1-yl)-3H-indeno[1,2-c]pyridazin-3-one, and Journal of Medicinal Chemistry (J. Med. Chem.), vol. 24, P. 830 (1981) discloses immunosuppressive 2-(4-chlorophenyl)benzothiopyrano[4,3-c]pyrazol-3-one and so on.

DISCLOSURE OF THE INVENTION

The present inventors have made intensive investigations in order to synthesize effective compounds and develop useful drugs, and then conceived a benzothiopyrano[4,3-c]pyridazine skeleton which has not been known in the prior art including the above-mentioned literatures.

As a result of such investigations, the present inventors have found that novel benzothiopyrano[4,3-c]pyridazine compounds of the following formula (I) possess useful activities such as anti-anxietic activity, and completed the present invention.

The present invention relates to benzothiopyran[4,3-c]pyridazine compounds of the formula:

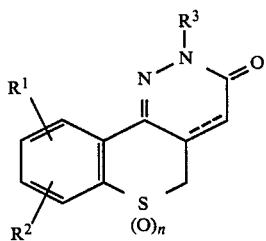

(I)

wherein $R^1$ and $R^2$ are the same or different and each is hydrogen, halogen, trifluoromethyl, hydroxy, amino, nitro, cyano, $C_{1-4}$ alkyl, $C_{1-4}$ alkoxy, or $C_{2-5}$ alkanoylamido, $R^3$ is hydrogen, $C_{1-8}$ alkyl, hydroxy-$C_{1-4}$ alkyl, $C_{2-5}$ alkanoyloxy-$C_{1-4}$ alkyl, pyridyl, aryl, aryl-$C_{1-4}$ alkyl, or aryl or aryl-$C_{1-4}$ alkyl substituted by at least one substituent selected from the group consisting of halogen, trifluoromethyl, hydroxy, amino, nitro, cyano, $C_{1-4}$ alkyl, $C_{1-4}$ alkoxy and $C_{2-5}$ alkanoylamido on the aromatic ring, n is 0, 1 or 2, and the bond ==== between the 4-position and the 4a-position is a single bond or double bond; and also relates to methods for preparing said compounds and pharmaceutical compositions containing said compounds.

In explaining each symbol of the formula (I) in accordance with the definitions, halogen includes fluorine, chlorine, bromine and iodine; $C_{1-4}$ alkyl includes, for example, methyl, ethyl, propyl, isopropyl, butyl, isobutyl and tert-butyl; $C_{1-4}$ alkoxy includes, for example, methoxy, ethoxy, propoxy, isopropoxy, butoxy, isobutoxy and tert-butoxy; $C_{2-5}$ alkanoylamido includes, for example, acetylamido, propionylamido, butyrylamido and pivaloylamido; hydroxy-$C_{1-4}$ alkyl includes, for example, hydroxymethyl, hydroxyethyl, hydroxypropyl and hydroxybutyl; $C_{2-5}$ alkanoyloxy-$C_{1-4}$ alkyl includes, for example, acetoxymethyl, acetoxyethyl, acetoxypropyl, acetoxybutyl, propionyloxymethyl, propionyloxyethyl, propionyloxypropyl and propionyloxybutyl; $C_{1-8}$ alkyl means straight or branched chain alkyl and includes, for example, methyl, ethyl, propyl, isopropyl, butyl, sec-butyl, tert-butyl, pentyl, isopentyl, neopentyl, hexyl, heptyl, octyl, 2-ethylhexyl, nonyl and decyl; aryl-$C_{1-4}$ alkyl includes, for example, benzyl, phenylethyl, phenylpropyl, phenylbutyl, naphthylmethyl, naphthylethyl, naphthylpropyl and naphthylbutyl; and aryl includes, for example, phenyl and naphthyl.

The compounds of the formula (I) having a chiral carbon atom can be prepared as a racemate or an optically active isomer, and the compound (I) having at least two chiral atoms can be obtained as an individual diastereomer or a mixture thereof. The present invention also embraces the mixture thereof and the individual isomers. Furthermore, the present invention embraces stereomers, too.

Preferred compounds of the formula (I) are the compounds wherein $R^1$ and $R^2$ are the same or different, and each is hydrogen, halogen, trifluoromethyl, hydroxy, amino, nitro, cyano, $C_{1-4}$ alkyl, $C_{1-4}$ alkoxy or $C_{2-5}$ alkanoylamido, $R^3$ is aryl or aryl substituted by at least one substituent selected from the group consisting of halogen, trifluoromethyl, hydroxy, nitro, $C_{1-4}$ alkyl and $C_{1-4}$ alkoxy on the aromatic ring, n is 0, 1 or 2, and the bond ==== between the 4-position and the 4a-position is a single bond or double bond.

More preferred compounds of the formula (I) are the compounds wherein $R^1$ and $R^2$ are the same or different and each is hydrogen, halogen or $C_{1-4}$ alkyl, $R_3$ is aryl or aryl substituted by at least one halogen on the aromatic ring, n is 0, 1 or 2, and the bond ==== between the 4-position and the 4a-position is a single bond.

The compounds of formula (I) of the present invention can be, for example, prepared by the methods described as follows.

Method (i)

A method which comprises reacting a compound of the formula:

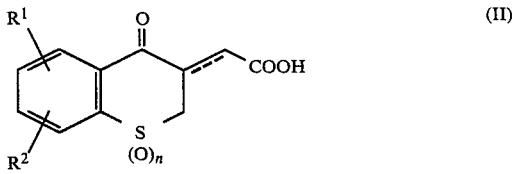

(II)

wherein each symbol is as defined above, with a hydrazine derivative of the formula:

$$R^3\text{---NHNH}_2 \qquad (III)$$

wherein $R^3$ is as defined above, a hydrate thereof or an acid addition salt thereof, and then subjecting the thus obtained compound of the formula:

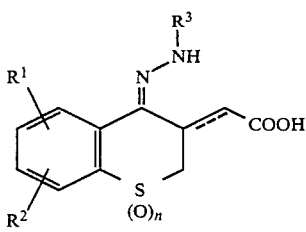

(IV)

wherein each symbol is as defined above, to a ring closure reaction.

The reaction is carried out by refluxing under heating for 5 to 20 hours in a suitable solvent, for example, in an alcoholic solvent such as methanol, ethanol or propanol to produce the compounds of formulas (I) and (IV).

When the hydrazine derivative of formula (III) is used in the form of the acid addition salt thereof, the above reaction is carried out in the presence of an acid scavenger (e.g. sodium acetate, potassium acetate, sodium hydrogencarbonate, sodium carbonate or potassium carbonate). The compound of the formula (IV), when obtained, is refluxed under heating in acetic acid for 5 to 10 hours to give the compound of formula (I).

Method (ii)

A method for preparing a compound of the formula (I) wherein n is 1 or 2, i.e. oxide or dioxide compound, which comprises subjecting a compound of the formula (I) wherein n is 0, to an oxidative reaction.

The reaction is carried out by keeping the reaction system at 10° to 100° C. for 1 to 10 hours in the presence of an oxidizing agent (e.g. peracetic acid, perbenzoic acid or m-chloroperbenzoic acid) in a suitable solvent. Being kept at room temperature for 1 to 5 hours in the presence of hydrogen peroxide in acetic acid as a solvent, the compound (I), wherein n is 1, can be preferentially prepared, while when keeping the reaction system at 30° to 100° C. for 2 to 10 hours, the compound (I) wherein n is 2 can be obtained.

Method (iii)

A method for preparing the compound (I) wherein $R^3$ is $C_{1-4}$ alkyl, hydroxy-$C_{1-4}$ alkyl, $C_{2-5}$ alkanoyloxy-$C_{1-4}$ alkyl or aryl-$C_{1-4}$ alkyl, by reacting a compound of the formula (I) wherein $R^3$ is hydrogen, with a compound of the formula:

$$R^4\text{-X} \quad \quad (V)$$

wherein $R^4$ is $C_{1-4}$ alkyl, hydroxy-$C_{1-4}$ alkyl, $C_{2-5}$ alkanoyloxy-$C_{1-4}$ alkyl or aryl-$C_{1-4}$ alkyl, and X is a reactive atom or group (e.g. halogen such as chlorine or bromine, or methanesulfonyloxy, toluenesulfonyloxy or benzenesulfonyloxy).

The reaction is carried out by keeping the reaction system at 0° to 50° C. for 1 to 10 hours in the presence of an acid scavenger (e.g. sodium hydride, sodium amide, sodium methoxide, sodium ethoxide, potassium hydroxide or sodium hydroxide) in a suitable solvent such as nonpolar solvent (e.g. benzene, toluene or xylene), or polar solvent (e.g. N,N-dimethylformamide or acetonitrile).

Method (iv)

A compound of the formula (I) wherein the bond between the 4-position and the 4a-position is a double bond, can be also prepared by adding bromine dropwise to the compound (I) wherein said bond is a single bond, in acetic acid, as described in Journal of Medicinal Chemistry (J. Med. Chem.) vol. 14, p. 262 (1971), or by reacting said compound with sodium m-nitrobenzenesulfonate (Bachmann Method) as described in British Pat. No. 1,168,291.

The reaction is preferably carried out by adding dropwise 1 to 1.5 times molar quantity of bromine to said compound in acetic acid.

Method (v)

A method which comprises converting the substituents $R^1$, $R^2$ or $R^3$ of the compounds obtained by the foregoing Methods (i) to (iv) into other substituents according to a conventional organic chemical synthesis.

Such methods include, for example, reduction of a nitro group to an amino group; acylation of an amino group with a lower alkanoic acid; and conversion of an amino group into a cyano group (e.g. Sandmeyer reaction or Gattermann reaction).

Each isomer can be isolated by the following conventional methods. In brief, a racemate can be divided into desired optically active isomers by means of a fractional recrystallization of a salt with an optically active acid, or by column chromatography using a column filled with an optically active carrier. Individual diastereomers can be separated by a method such as fractional crystallization or chromatography. Such compounds can also be obtained by using an optically active starting material. Furthermore, the stereomers can be isolated by a method such as recrystallization or column chromatography.

The compounds of the formula (II) of the present invention are novel compounds and can be prepared, for example, by adding methyl iodide to the compound of formula:

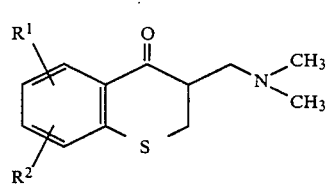

(VI)

wherein each symbol is as defined above, in acetone; maintaining the mixture at room temperature for 2 to 5 hours to produce a quaternary ammonium compound; adding potassium cyanide or sodium cyanide in methanol or dimethylformamide; stirring at 40°–50° C. for 4 to 8 hours to produce a cyano compound of the formula:

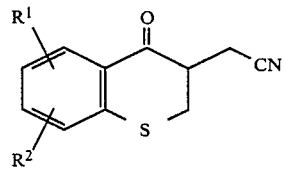

(VII)

wherein each symbol is as defined above; adding acetic acid and concentrated hydrochloric acid thereto; and maintaining the reaction mixture at 80°–100° C. for 8 to 10 hours to give the compound of formula:

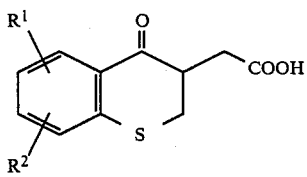

(II')

wherein each symbol is as defined above.

For reference, representative compounds of the formula (VII) and (II') with their physical constants are shown as follows:

Compound (VII)

α-(6-chloro-2,3-dihydro-4-oxo-4H-1-benzothiopyran-3-yl)acetonitrile, melting at 148°–150° C.
α-(2,3-dihydro-6-methyl-4-oxo-4H-1-benzothiopyran-3-yl)acetonitrile, melting at 114°–116° C.

Compound (II')

α-(2,3-dihydro-4-oxo-4H-1-benzothiopyran-3-yl)acetic acid, melting at 110°–113° C.
α-(6-chloro-2,3-dihydro-4-oxo-4H-1-benzothiopyran-3-yl)acetic acid, melting at 167°–169° C.
α-(2,3-dihydro-6-fluoro-4-oxo-4H-1-benzothiopyran-3-yl)acetic acid, melting at 141°–143° C.
α-(2,3-dihydro-4-oxo-6-methyl-4H-1-benzothiopyran-3-yl)acetic acid, melting at 113°–115° C.

The compounds of the formula (I) of the present invention are useful as anti-anxiety agents because they possess antagonistic activity to the chemical inducer of convulsion such as bicuculline or pentylenetetrazole and exhibit high affinity of from $10^{-6}$ to $10^{-8}$M for the benzodiazepine receptor and, on the contrary, they have less effect on the somatic function such as muscular relaxation activity. They are also useful as neutralizers to an excess dose or a poisoning of the existing anti-anxiety agents such as diazepam.

Pharmacological activities of the compounds of the present invention together with their experimental methods are shown as follows:

(1) Displacement ability for benzodiazepine receptor
Experiment on the specific binding for benzodiazepine receptor The experiment was performed according to the methods described in European Journal of Pharmacology, vol. 51, P. 129 (1978) and Life Science, vol. 20, p. 1201 (1977).

In brief, a crude synaptosomal fraction was isolated from the cerebral cortex of 9 to 10 week-old male Wistar rats and suspended in 50 mM of Tris-hydrochloric acid buffer solution (pH 7.4) containing 120 mM of sodium chloride and 5 mM of potassium chloride.

To the synaptosomal suspension as prepared above were added various concentrations of test compounds and tritiated diazepam (final concentration:2 nM), and the mixture was incubated at 0° C. for 20 minutes. Then the suspension was filtered through Whatman GF/B glass fiber filter. After the filter was washed with the foregoing buffer solution, the radioactivity left on the filter was measured by a liquid scintillation spectrometry.

Specific binding was determined by subtracting binding in the presence of $10^{-6}$M unlabelled diazepam from total binding.

According to the above experimental method, the affinity of the compounds of the present invention for benzodiazepine receptor is evaluated as an ability to displace tritiated diazepam from the binding site, and is represented as Ki value.

The results are summarized in the Table 1.

TABLE 1

| Test compound (Example No.) | binding for benzodiazepine $K_i$(nM) |
| --- | --- |
| 1 | 40 |
| 9 | 12 |
| 10 | 13 |
| 13 | 45 |

(2) Anti-bicuculline effect

The experiment of anti-bicuculline effect was performed according to the method described in Life Science, vol. 21, p. 1779 (1977).

In brief, groups of 7–14 male ddY-strain mice weighing 20–28 g were used. (+)Bicuculline (0.6 mg/kg) was intraveneously administered 1 hour after the oral adminstration of test compound, and the $ED_{50}$, 50% effective dose, was determined by observing the existence of tonic convulsion within 5 minutes.

The results are summarized in the Table 2.

TABLE 2

| Test compound (Example No.) | Anti-bicuculline effect ($ED_{50}$, mg/kg p.o.) |
| --- | --- |
| 1 | 12.4 |
| 3 | 4.1 |
| 19 | 10.6 |
| 23 | 40.6 |

The compounds of the present invention, when used as drugs, can be administered in the form of tablets, capsules, granules, syrup, injectable solutions, suppositories, powder or the like by mixing with pharmacologically acceptable excipient, carrier, diluent and so on. The daily dose, for example, in an oral administration for human adults usually ranges from 5 mg to 500 mg in a single or multiple doses.

The present invention will be explained by the following examples in more detail.

EXAMPLE 1

A mixture of 10 g of α-(2,3-dihydro-4-oxo-4H-1-benzothiopyran-3-yl)acetic acid, 12 g of 4-chlorophenyhydrazine hydrochloride and 5.5 g of sodium acetate in 200 ml of ethanol is refluxed under heating for 10 hours. The ethanol is distilled off under reduced pressure and to the residue is added 200 ml of acetic acid and the mixture is refluxed under heating for 10 hours. After the acetic acid is distilled off, the residue is extracted with chloroform. The extract is washed with water, dried over magnesium sulfate anhydride and the chloroform is distilled off under reduced pressure. To the precipitated crystals is added diisopropyl ether. The crystals are collected by filtration and recrystallized from acetic acid to give 11.5 g of 2-(4-chlorophenyl)-2,3,4,4a-tetrahydro-5H-(1)benzothiopyrano[4,3-c]pyridazin-3-one, melting at 146°–147° C., as colorless prisms.

EXAMPLE 2

A mixture of 2 g of α-(2,3-dihydro-4-oxo-6-methyl-4H-1-benzothiopyran-3-yl)acetic acid and 0.8 g of 100% hydrazine hydrate in 50 ml of ethanol is refluxed under heating for 8 hours. After about half the volume of ethanol is distilled off under reduced pressure and the residue is allowed to cool, the precipitated crystals are collected by filtration and recrystallized from acetic acid to give 1 g of 9-methyl- 2,3,4,4a-tetrahydro-5H-(1)benzothiopyrano[4,3-c]pyridazin 3-one, melting at 217°–219° C., as colorless prisms.

EXAMPLE 3

To a mixture of 11.5 g of 2-(4-chlorophenyl)-2,3,4,4a-tetrahydro-5H-(1)benzothiopyrano[4,3-c]pyridazin-3-one in 200 ml of acetic acid is added 66 ml of 35% hydrogen peroxide dropwise with stirring at room temperature. After the completion of addition, the mixture is stirred at room temperature for 3 hours, poured into an excess amount of water and extracted with chloroform. The extract is washed with water, dried over magnesium sulfate anhydride and the chloroform is distilled off under reduced pressure. To the precipitated crystals is added diisopropyl ether. The crystals are collected by filtration and recrystallized from isopropyl alcohol to give 7.7 g of 2-(4-chlorophenyl)-2,3,4,4a-tetrahydro-5H-(1)benzothiopyrano[4,3-c]pyridazin-3-one 6-oxide, melting at 181°–183° C., as colorless needles.

EXAMPLE 4

2-(4-Chlorophenyl)-2,3,4,4a-tetrahydro-5H-(1)benzothiopyrano[4,3-c]pyridazin-3-one 6-oxide (7.0 g) prepared in Example 3 is separated and purified by using column chromatography on silica gel with a mixture of hexane and ethyl acetate (3:1) as an eluent. The crystals obtained from the first fraction of the eluate are recrystallized from isopropyl alcohol to give 0.6 g of (4aR*, 6S*)-2-(4-chlorophenyl)-2,3,4,4a-tetrahydro-5H-(1)benzothiopyrano[4,3-c]pyridazin-3-one 6-oxide, melting at 210°–213° C. And also, the crystals obtained from the second fraction of the eluate are recrystallized from isopropyl alcohol to give 5.0 g of (4aR*, 6R*)-2-(4-chlorophenyl)-2,3,4,4a-tetrahydro-5H-(1)benzothiopyrano[4,3-c]pyridazin-3-one 6-oxide, melting at 190°–192° C.

EXAMPLE 5

To a mixture of 4.7 g of 2-(4-chlorophenyl)-2,3,4,4a-tetrahydro-5H-(1)benzothiopyrano[4,3-c]pyridazin-3-one 6-oxide in 150 ml of acetic acid is added 55 ml of 35% hydrogen peroxide dropwise with stirring at room temperature. After the completion of addition, the mixture is stirred at 40°–50° C. on a water bath for 4 hours and poured into an excess amount of water. The precipitated crystals are collected by filtration and recrystallized from 50% aqueous solution of acetic acid to give 2.9 g of 2-(4-chlorophenyl)-2,3,4,4a-tetrahydro-5H-(1)benzothiopyrano[4,3-c]pyridazin-3-one 6,6-dioxide, melting at 168°–170° C., as a colorless powder.

EXAMPLE 6

To a mixture of 2 g of α-(2,3-dihydro-6-fluoro-4-oxo-4H-1-benzothiopyran-3-yl)acetic acid in 20 ml of N,N-dimethylformamide is added 0.4 g of 60% sodium hydride with stirring. After the mixture is stirred at 40°–50° C. on a water bath for 1 hour, the mixture is cooled to room temperature and to the mixture is added 2.4 g of methyl iodide. The mixture is stirred at about 30° C. on a water bath for 3 hours and subjected to distillation under reduced pressure and then the residue is extracted with chloroform. The extract is washed with water and dried over magnesium sulfate anhydride. The chloroform is distilled off under reduced pressure, and to the precipitated crystals is added diisopropyl ether. The crystals are collected by filtration and recrystallized from ethanol to give 1 g of 9-fluoro-2-methyl-2,3,4,4a-tetrahydro-5H-(1)benzothiopyrano[4,3-c]pyridazin-3-one, melting at 125°–128° C., as colorless prisms.

EXAMPLE 7

To a mixture of 1.7 g of 2-(4-chlorophenyl)-9-methyl-2,3,4,4a-tetrahydro-5H-(1)benzothiopyrano[4,3-c]pyridazin-3-one in 30 ml of acetic acid is added 1.2 g of bromine dropwise with stirring at 40°–50° C. on a water bath. After the completion of addition, the mixture is stirred at 50° C. for 3 hours and poured into an excess amount of water. The precipitated crystals are collected by filtration and recrystallized from acetic acid to give 0.5 g of 2-(4-chlorophenyl)-9-methyl-2,3-dihydro-5H-(1)benzothiopyrano[4,3-c]pyridazin-3-one, melting at 200°–206° C., as a yellow powder.

The following compounds can be prepared in a similar manner as the above Examples.

EXAMPLE 8

2-phenyl-2,3,4,4a-tetrahydro-5H-(1)benzothiopyrano[4,3-c]pyridazin-3-one, melting at 103°–106° C.

EXAMPLE 9

2-(4-methylphenyl)-2,3,4,4a-tetrahydro-5H-(1)benzothiopyrano[4,3-c]pyridazin-3-one, melting at 116°–118° C.

EXAMPLE 10

2-(4-methoxyphenyl)-2,3,4,4a-tetrahydro-5H-(1)benzothiopyrano[4,3-c]pyridazin-3-one, melting at 116°–118° C.

EXAMPLE 11

2-(3,4-dichlorophenyl)-2,3,4,4a-tetrahydro-5H-(1)benthiopyrano[4,3-c]pyridazin-3-one, melting at 163°–165° C.

EXAMPLE 12

2-(3,4-dichlorophenyl)-2,3,4,4a-tetrahydro-5H-(1)benzothiopyrano[4,3-c]pyridazin-3-one 6-oxide, melting at 184°–187° C.

EXAMPLE 13

2-(4-bromophenyl)-2,3,4,4a-tetrahydro-5H-(1)benzothiopyrano[4,3-c]pyridazin-3-one, melting at 167°–169° C.

EXAMPLE 14

9-chloro-2-(4-fluorophenyl)-2,3,4,4a-tetrahydro-5H-(1)benzothiopyrano[4,3-c]pyridazin-3-one, melting at 130°–131° C.

EXAMPLE 15

9-chloro-2-(4-chlorophenyl)-2,3,4,4a-tetrahydro-5H-(1)benzothiopyrano[4,3-c]pyridazin-3-one, melting at 134°–136° C.

EXAMPLE 16

9-chloro-2-(4-fluorophenyl)-2,3,4,4a-tetrahydro-5H-(1)benzothiopyrano[4,3-c]pyridazin-3-one 6-oxide, melting at 241°–243° C. with decomposition

EXAMPLE 17

9-chloro-2-(4-chlorophenyl)-2,3,4,4a-tetrahydro-5H-(1)benzothiopyrano[4,3-c]pyridazin-3-one 6-oxide, melting at 209°–211° C.

EXAMPLE 18

2-(4-chlorophenyl)-9-fluoro-2,3,4,4a-tetrahydro-5H-(1)benzothiopyrano[4,3-c]pyridazin-3-one, melting at 253°–256° C.

EXAMPLE 19

2-(4-chlorophenyl)-9-fluoro-2,3,4,4a-tetrahydro-5H-(1)benzothiopyrano[4,3-c]pyridazin-3-one 6-oxide, melting at 188°–191° C.

EXAMPLE 20

9-fluoro-2-(3-trifluoromethylphenyl)-2,3,4,4a-tetrahydro-5H-(1)benzothiopyrano[4,3-c]pyridazin-3-one, melting at 192°–194° C.

EXAMPLE 21

9-fluoro-2-(4-nitrophenyl)-2,3,4,4a-tetrahydro-5H-(1)benzothiopyrano[4,3-c]pyridazin-3-one, melting at 188°–190° C.

EXAMPLE 22

2-(4-methoxyphenyl)-9-methyl-2,3,4,4a-tetrahydro-5H-(1)benzothiopyrano[4,3-c]pyridazin-3-one, melting at 146°–148° C.

EXAMPLE 23

2-(4-chlorophenyl)-9-methyl-2,3,4,4a-tetrahydro-5H-(1)benzothiopyrano[4,3-c]pyridazin-3-one 6-oxide, melting at 186°–189° C.

EXAMPLE 24

2-(4-chlorophenyl)-9-methyl-2,3,4,4a-tetrahydro-5H-(1)benzothiopyrano[4,3-c]pyridazin-3-one, melting at 169°–171° C.

EXAMPLE 25

2-(4-chlorophenyl)-9-methyl-2,3,4,4a-tetrahydro-5H-(1)benzothiopyrano[4,3-c]pyridazin-3-one 6,6-dioxide, melting at 164°–167° C.

EXAMPLE 26

9-chloro-2,3,4,4a-tetrahydro-5H-(1)benzothiopyrano[4,3-c]pyridazin-3-one, melting at 211°–212° C.

EXAMPLE 27

2-(2-acetoxyethyl)-2,3,4,4a-tetrahydro-5H-(1)-benzothiopyrano[4,3-c]pyridazin-3-one, melting at 82°–86° C.

EXAMPLE 28

9-fluoro-2,3,4,4a-tetrahydro-5H-(1)benzothiopyrano[4,3-c]pyridazin-3-one, melting at 226°–228° C.

EXAMPLE 29

2-(4-bromophenyl)-2,3,4,4a-tetrahydro-5H-(1)benzothiopyrano[4,3-c]pyridazin-3-one 6-oxide, melting at 204°–206° C.

EXAMPLE 30

2-(3,4-dichlorophenyl)-2,3,4,4a-tetrahydro-5H-(1)benzothiopyrano[4,3-c]pyridazin-3-one 6,6-dioxide, melting at 165°–166° C.

EXAMPLE 31

2-(4-trifluoromethylphenyl)-2,3,4,4a-tetrahydro-5H-(1)benzothiopyrano[4,3-c]pyridazin-3-one, melting at 124°–127° C.

EXAMPLE 32

2-(4-hydroxyphenyl)-2,3,4,4a-tetrahydro-5H-(1)benzothiopyrano[4,3-c]pyridazin-3-one, melting at 239°–240° C.

EXAMPLE 33

2-(2-pyridyl)-2,3,4,4a-tetrahydro-5H-(1)benzothiopyrano[4,3-c]pyridazin-3-one, melting at 125°–129° C.

EXAMPLE 34

2-(4-chlorophenyl)-2,3-dihydro-5H-(1)benzothiopyrano[4,3-c]pyridazin-3-one 6-oxide, melting at 195°–196° C.

EXAMPLE 35

2-(4-chlorophenyl)-9-methoxy-2,3,4,4a-tetrahydro-5H-(1)benzothiopyrano[4,3-c]pyridazin-3-one, melting at 143°–144° C.

EXAMPLE 36

2-(4-chlorophenyl)-9-hydroxy-2,3,4,4a-tetrahydro-5H-(1)benzothiopyrano[4,3-c]pyridazin-3-one, melting at 214°–215° C.

EXAMPLE 37

2-(4-chlorophenyl)-2,3-dihydro-5H-(1)benzothiopyrano[4,3-c]pyridazin-3-one, melting at 183°–185° C.

EXAMPLE 38

2-(4-methoxyphenyl)-9-methoxy-2,3,4,4a-tetrahydro-5H-(1)benzothiopyrano[4,3-c]pyridazin-3-one, melting at 124°–126° C.

EXAMPLE 39

9-fluoro-2-(3-trifluoromethylphenyl)-2,3,4,4a-tetrahydro-5H-(1)benzothiopyrano[4,3-c]pyridazin-3-one 6,6dioxide, melting at 150°–153° C.

EXAMPLE 40

2-(3-chlorophenyl)-2,3,4,4a-tetrahydro-5H-(1)benzothiopyrano[4,3-c]pyridazin-3-one, melting at 136°–138° C.

EXAMPLE 41

2-(3-chlorophenyl)-2,3,4,4a-tetrahydro-5H-(1)benzothiopyrano[4,3-c]pyridazin-3-one 6,6-dioxide, melting at 175°–177° C.

EXAMPLE 42

2-(4-chlorophenyl)-7-chloro-2,3,4,4a-tetrahydro-5H-(1)benzothiopyrano[4,3-c]pyridazin-3-one, melting at 195°–196° C.

EXAMPLE 43

9-fluoro-2-(3-trifluoromethylphenyl)-2,3,4,4a-tetrahydro-5H-(1)benzothiopyrano[4,3-c]pyridazin-3-one 6-oxide, melting at 170°–173° C.

EXAMPLE 44

2-(2-chlorophenyl)-2,3,4,4a-tetrahydro-5H-(1)benzothiopyrano[4,3-c]pyridazin-3-one, melting at 165°–167° C.

EXAMPLE 45

9-methoxy-2-(3-trifluoromethylphenyl)-2,3,4,4a-tetrahydro-5H-(1)benzothiopyrano[4,3-c]pyridazin-3-one, melting at 149°–151° C.

EXAMPLE 46

9-hydroxy-2-(3-trifluoromethylphenyl)-2,3,4,4a-tetrahydro-5H-(1)benzothiopyrano[4,3-c]pyridazin-3-one, melting at 222°–223° C.

EXAMPLE 47

9-fluoro-2-(4-methoxyphenyl)-2,3,4,4a-tetrahydro-5H-(1)benzothiopyrano[4,3-c]pyridazin-3-one, melting at 123°–125° C.

EXAMPLE 48

9-fluoro-2-(4-hydroxyphenyl)-2,3,4,4a-tetrahydro-5H-(1)benzothiopyrano[4,3-c]pyridazin-3-one, melting at 261°–262° C.

EXAMPLE 49

2-(4-trifluoromethylphenyl)-2,3,4,4a-tetrahydro-5H-(1)benzothiopyrano[4,3-c]pyridazin-3-one 6-oxide

EXAMPLE 50

2-(4-fluorophenyl)-2,3,4,4a-tetrahydro-5H-(1)benzothiopyrano[4,3-c]pyridazin-3-one

EXAMPLE 51

2-(4-fluorophenyl)-2,3,4,4a-tetrahydro-5H-(1)benzothiopyrano[4,3-c]pyridazin-3-one 6-oxide

EXAMPLE 52

2-(4-aminophenyl)-2,3,4,4a-tetrahydro-5H-(1)benzothiopyrano[4,3-c]pyridazin-3-one

EXAMPLE 53

2-(4-acetylamidophenyl)-2,3,4,4a-tetrahydro-5H-(1)benzothiopyrano[4,3-c]pyridazin-3-one

EXAMPLE 54

2-(4-propionylamidophenyl)-2,3-dihydro-5H-(1)benzothiopyrano[4,3-c]pyridazin-3-one

EXAMPLE 55

2-(4-trifluoromethylphenyl)-9-methoxy-2,3,4,4a-tetrahydro-5H-(1)benzothiopyrano[4,3-c]pyridazin-3-one

EXAMPLE 56

2-(4-chlorophenyl)-9-nitro-2,3,4,4a-tetrahydro-5H-(1)benzothiopyrano[4,3-c]pyridazin-3-one

EXAMPLE 57

9-acetylamido-2-(4-chlorophenyl)-2,3,4,4a-tetrahydro-5H-(1)benzothiopyrano[4,3-c]pyridazin-3-one

EXAMPLE 58

2-phenyl-8-trifluoromethyl-2,3,4,4a-tetrahydro-5H-(1)benzothiopyrano[4,3-c]pyridazin-3-one

EXAMPLE 59

8,9-dimethyl-2,3,4,4a-tetrahydro-5H-(1)benzothiopyrano[4,3-c]pyridazin-3-one

EXAMPLE 60

2-butyl-2,3,4,4a-tetrahydro-5H-(1)benzothiopyrano[4,3-c]pyridazin-3-one

EXAMPLE 61

2-(3-hydroxypropyl)-2,3,4,4a-tetrahydro-5H-(1)benzothiopyrano[4,3-c]pyridazin-3-one

EXAMPLE 62

9-amino-2-phenyl-2,3,4,4a-tetrahydro-5H-(1)benzothiopyrano[4,3-c]pyridazin-3-one

EXAMPLE 63

2-(4-chlorophenyl)-2,3-dihydro-5H-(1)benzothiopyrano[4,3-c]pyridazin-3-one 6,6-dioxide

EXAMPLE 64

2-benzyl-2,3,4,4a-tetrahydro-5H-(1)benzothiopyrano[4,3-c]pyridazin-3-one

EXAMPLE 65

2-(3-phenylpropyl)-2,3,4,4a-tetrahydro-5H-(1)benzothiopyrano[4,3-c]pyridazin-3-one

EXAMPLE 66

2-octyl-2,3,4,4a-tetrahydro-5H-(1)benzothiopyrano[4,3-c]pyridazin-3-one

EXAMPLE 67

2-(4-chlorophenyl)-9-cyano-2,3,4,4a-tetrahydro-5H-(1)benzothiopyrano[4,3-c]pyridazin-3-one

EXAMPLE 68

2-(4-cyanophenyl)-2,3,4,4a-tetrahydro-5H-(1)benzothiopyrano[4,3-c]pyridazin-3-one Although the present invention has been adequately discussed in the foregoing specification and examples included therein, one readily recognizes that various changes and modifications may be made without departing from the spirit and scope of the present invention.

We claim:

1. A benzothiopyrano[4,3-C]pyridazine compound of the formula:

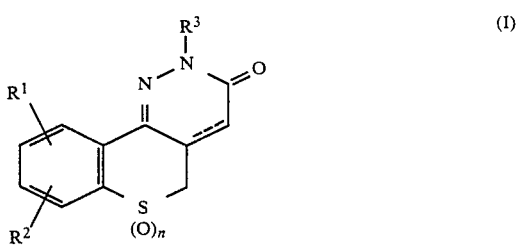

(I)

wherein $R^1$ and $R^2$ are the same or different and each is hydrogen, halogen, trifluoromethyl, hydroxy, amino, nitro, cyano, $C_{1-4}$ alkyl, $C_{1-4}$ alkoxy or $C_{2-5}$ alkanoylamido, with the proviso that $R^1$ and $R^2$ are not hydroxy and $C_{1-4}$ alkoxy at the same time, $R^3$ is hydrogen, $C_{1-8}$ hydroxy-$C_{1-4}$ alkyl, $C_{2-5}$ alkanoyloxy-$C_{1-4}$ alkyl, pyridyl, phenyl, naphthyl, phenyl-$C_{1-4}$ alkyl, or naphthyl-$C_{1-4}$ alkyl wherein said phenyl, naphthyl, phenyl-$C_{1-4}$ alkyl and naphthyl-$C_{1-4}$ alkyl groups are each unsubstituted or substituted by one or two substituents selected from the group consisting of halogen, triguloromethyl, hydroxy, amino, nitro, cyano, $C_{1-4}$ alkyl, $C_{1-4}$ alkoxy and $C_{2-5}$ alkanoylamido on the aromatic ring, n is 0, 1 or 2, and the bond ==== between the 4-position and the 4a-position is a single bond or double bond.

2. A compound of claim 1 wherein $R^3$ is phenyl or naphthyl which is unsubstituted or substituted by one or two substituents selected from the group consisting of halogen, trifluoromethyl, hydroxy, nitro, $C_{1-4}$ alkyl and $C_{1-4}$ alkoxy.

3. A compound of claim 1 wherein $R^1$ and $R^2$ are the same or different and each is hydrogen, halogen or $C_{1-4}$ alkyl, $R^3$ is phenyl or naphthyl which is unsubstituted or substituted by one or two halogens, and the bond ==== between the 4-position and the 4a-position is a single bond.

4. A compound of claim 1 selected from 2-(4-chlorophenyl)-2,3,4,4a-tetrahydro-5H-(1)benzothiopyrano[4,3-c]pyridazin-3-one 6-oxide, (4aR*,6R*)-2-(4-chlorophenyl)-2,3,4,4a-tetrahydro-5H-(1)benzothiopyrano[4,3-c]pyridazin-3-one 6-oxide, (4aR*, 6S*)-2-(4-chlorophenyl)-2,3,4,4a-tetrahydro-5H-(1)benzothiopyrano[4,3-c]pyridazin-3-one 6-oxide, 2-(4-chlorophenyl)-9-fluoro-2,3,4,4a-tetrahydro-5H-(1)benzothiopyrano[4,3-c]pyridazin-3-one 6-oxide, 2-(4-chlorophenyl)-2,3,4,4a-tetrahydro-5H-(1)benzothiopyrano[4,3-c]pyridazin-3-one, 2-(4-bromophenyl)-2,3,4,4a-tetrahydro-5H-(1)benzothiopyrano[4,3-c]pyridazin-3-one 6-oxide, 2-(4-chlorophenyl)-2,3,4,4a-tetrahydro-5H-(1)benzothiopyrano[4,3-c]pyridazin-3-one 6,6-dioxide and 2-(4-chlorophenyl)-9-methyl-2,3,4,4a-tetrahydro-5H-(1)benzothiopyrano[4,3-c]pyridazin-3-one 6-oxide.

5. A pharmaceutical composition for use as an antianxietic agent, comprising a therapeutically effective amount of a compound of claim 1, and a pharmaceutically acceptable additive.

* * * * *